(12) United States Patent
Wang et al.

(10) Patent No.: US 12,175,669 B2
(45) Date of Patent: Dec. 24, 2024

(54) METHOD AND APPARATUS FOR ACQUIRING CONTOUR LINE OF BLOOD VESSEL ACCORDING TO CENTERLINE OF BLOOD VESSEL

(71) Applicant: SUZHOU RAINMED MEDICAL TECHNOLOGY CO., LTD., Suzhou (CN)

(72) Inventors: Zhiyuan Wang, Suzhou (CN); Guangzhi Liu, Suzhou (CN); Wenbin Cao, Suzhou (CN); Xinyu Wu, Suzhou (CN)

(73) Assignee: SUZHOU RAINMED MEDICAL TECHNOLOGY CO., LTD., Suzhou (CN)

( * ) Notice: Subject to any disclaimer, the term of this patent is extended or adjusted under 35 U.S.C. 154(b) by 381 days.

(21) Appl. No.: 17/746,087

(22) Filed: May 17, 2022

(65) Prior Publication Data
US 2022/0277447 A1 Sep. 1, 2022

Related U.S. Application Data

(63) Continuation of application No. PCT/CN2019/120333, filed on Nov. 22, 2019.

(30) Foreign Application Priority Data

Nov. 19, 2019 (CN) .......................... 201911135307.1

(51) Int. Cl.
*G06K 9/00* (2022.01)
*A61B 5/02* (2006.01)
(Continued)

(52) U.S. Cl.
CPC ........ *G06T 7/0012* (2013.01); *A61B 5/02007* (2013.01); *A61B 6/504* (2013.01);
(Continued)

(58) Field of Classification Search
CPC ........... G06T 7/0012; G06T 7/66; G06T 7/13; G06T 2207/30048; G06T 2207/30101;
(Continued)

(56) References Cited

U.S. PATENT DOCUMENTS 6,501,848 B1  12/2002  Carroll et al.
7,369,691 B2   5/2008  Kondo et al.
(Continued)

FOREIGN PATENT DOCUMENTS

CN    102346803 A    2/2012
CN    106127819 A   11/2016
(Continued)

OTHER PUBLICATIONS

Wang, Shyh Roei, et al. "Dual snake-based vessel wall detection for MSCT coronary artery analysis." Journal of Medical and Biological Engineering 27.4 (2007): 165-171. (Year: 2007).*
(Continued)

*Primary Examiner* — Avinash Yentrapati
(74) *Attorney, Agent, or Firm* — Ladas & Parry LLP (57) ABSTRACT

The present disclosure provides a method and an apparatus for acquiring a contour line of a blood vessel according to a centerline of the blood vessel. The method comprises: extracting a centerline of a blood vessel according to a two-dimensional coronary artery angiogram image (S100); obtaining an image of a straightened blood vessel according to the centerline of the blood vessel (S200); setting a threshold $D_{threshold}$ for a diameter of the blood vessel on the image of the straightened blood vessel (S300); generating a preset contour line of the blood vessel on both sides of a centerline of the straightened blood vessel according to the $D_{threshold}$ (S400); making the preset contour line of the blood vessel step-by-step approach the centerline of the straightened blood vessel to acquire a contour line of the straight-
(Continued)

ened blood vessel (S500); projecting the contour line of the straightened blood vessel back onto the image of the centerline of the blood vessel to obtain a contour line of the blood vessel (S600).

13 Claims, 6 Drawing Sheets

(51) Int. Cl.
  *A61B 6/50* (2024.01)
  *G06T 7/00* (2017.01)
  *G06T 7/13* (2017.01)
  *G06T 7/66* (2017.01)

(52) U.S. Cl.
  CPC .................. *G06T 7/13* (2017.01); *G06T 7/66* (2017.01); *G06T 2207/30048* (2013.01); *G06T 2207/30101* (2013.01)

(58) Field of Classification Search
  CPC . G06T 2207/20021; G06T 2207/20156; G06T 2207/30172; G06T 7/181; A61B 5/02007; A61B 6/504; A61B 5/004; A61B 6/5217
  See application file for complete search history.

(56) References Cited

U.S. PATENT DOCUMENTS

| | | | |
|---|---|---|---|
| 10,452,813 | B2 | 10/2019 | Sorenson et al. |
| 2015/0235360 | A1 | 8/2015 | Zheng et al. |
| 2016/0239956 | A1* | 8/2016 | Kang ................... A61B 6/5247 |
| 2019/0318476 | A1* | 10/2019 | Isgum ................... G16H 50/50 |

FOREIGN PATENT DOCUMENTS

| | | |
|---|---|---|
| CN | 106327487 A | 1/2017 |
| CN | 108805815 A | 11/2018 |
| CN | 109461138 A | 3/2019 |
| EP | 3503026 | 6/2019 |

OTHER PUBLICATIONS

Yang, Guanyu, et al. "Quantitative measurement of coronary artery stenosis in CCTA images using a 2D parametric intensity model." 2014 36th Annual International Conference of the IEEE Engineering in Medicine and Biology Society. IEEE, 2014. (Year: 2014).*
ISR for International Application PCT/CN2019/120333 mailed Aug. 19, 2020.
Written Opinion for International Application PCT/CN2019/120333 mailed Aug. 19, 2020.
G. Yang et al., "Quantitative measurement of coronary artery stenosis in CCTA images using a 2D parametric intensity model," 2014 36th Annual International Conference of the IEEE Engineering in Medicine and Biology Society, Chicago, IL, USA, 2014, pp. 1071-1074, doi: 10.1109/EMBC.2014.6943779.
Wang, S. R. et al., (2007). Dual snake-based vessel wall detection for MSCT coronary artery analysis. Journal of Medical and Biological Engineering, 27(4), 165-171.
Extended European Search Report for Application No. PCT/CN2019/120333, dated Nov. 2, 2023, 11 pages.

* cited by examiner

METHOD AND APPARATUS FOR ACQUIRING CONTOUR LINE OF BLOOD VESSEL ACCORDING TO CENTERLINE OF BLOOD VESSEL

CROSS REFERENCE TO RELATED APPLICATION

This application is a continuation of International Patent Application No. PCT/CN2019/120333 filed on Nov. 22, 2019. The disclosure claims priority to Chinese Patent Application No. 201911135307.1 filed before Chinese National Intellectual Property Administration on Nov. 19, 2019, entitled "METHOD AND APPARATUS FOR ACQUIRING CONTOUR LINE OF BLOOD VESSEL ACCORDING TO CENTERLINE OF BLOOD VESSEL", the entire contents of which are hereby incorporated by reference.

FIELD OF THE DISCLOSURE

The present disclosure relates to the field of coronary artery medical technology, and in particular to a method and an apparatus for acquiring a contour line of a blood vessel according to a centerline of the blood vessel, a coronary artery analysis system and a computer storage medium.

BACKGROUND

The deposition of lipids and saccharides in human blood on blood vessels walls will form plaques on the blood vessels walls, and in turn lead to vascular stenosis. The vascular stenosis, especially near the coronary arteries of the heart, will lead to insufficient blood supply to the cardiac muscle and induce diseases such as coronary heart disease and angina pectoris, posing a serious threat to human health. According to statistics, there are about 11 million patients suffering from the coronary heart disease in China, and the number of patients treated with cardiovascular interventional surgery is increasing by more than 10% every year.

Although conventional medical detection methods such as coronary angiography (CAG) and computed tomography (CT) can display the severity of coronary artery stenosis of the heart, they cannot accurately evaluate ischemic conditions of coronary arteries. In order to improve the accuracy of coronary vascular function evaluation, in 1993, Pijls proposed a new indicator for concluding coronary vascular function from pressure measurement—Fractional Flow Reserve (FFR). After long-term basic and clinical research, FFR has become a golden standard for functional evaluation of coronary stenosis.

Fractional Flow Reserve (FFR) usually refers to the fractional flow reserve of the cardiac muscle, and is defined as a ratio of the maximum blood flow that the diseased coronary artery can provide to the cardiac muscle to the maximum blood flow provided by the completely normal coronary artery. A study shows that in the maximum hyperemia state of the coronary artery, the ratio of blood flows can be replaced by the pressure value. That is to say, a FFR value can be measured and then calculated by measuring a pressure at a distal end of the coronary artery stenosis and a pressure at a proximal end of the coronary artery stenosis via a pressure sensor in the maximum hyperemia state of the coronary artery.

In the prior art, when calculating blood vessel evaluation parameters through a three-dimensional model of a blood vessel, it is often necessary to extract a contour line of the blood vessel. Due to the presence of curling and unclear edges of the blood vessel, it is particularly difficult to extract the contour line of the blood vessel, and calculation data is large and tedious. Therefore, how to quickly extract the contour line of the blood vessel and how to improve the accuracy of extraction have always been problems that need to be solved by those skilled in the art.

SUMMARY

The present disclosure provides a method and an apparatus for acquiring a contour line of a blood vessel according to a centerline of the blood vessel, a coronary artery analysis system and a computer storage medium, so as to solve the problems of how to quickly extract the contour line of the blood vessel and how to improve accuracy of extraction, which always need to be solved by those skilled in the art.

In order to achieve the above object, in a first aspect, the disclosure provides a method for acquiring a contour line of a blood vessel according to a centerline of the blood vessel, comprising:

extracting a centerline of a blood vessel according to a two-dimensional coronary artery angiogram image;

obtaining an image of a straightened blood vessel according to the centerline of the blood vessel;

setting a threshold $D_{threshold}$ for a diameter of the blood vessel on the image of the straightened blood vessel;

generating a preset contour line of the blood vessel on both sides of a centerline of the straightened blood vessel according to the $D_{threshold}$;

making the preset contour line of the blood vessel step-by-step approach the centerline of the straightened blood vessel to acquire a contour line of the straightened blood vessel;

projecting the contour line of the straightened blood vessel back onto the image of the centerline of the blood vessel to obtain a contour line of the blood vessel.

Optionally, in the above method for acquiring a contour line of a blood vessel according to a centerline of the blood vessel, a manner for obtaining an image of a straightened blood vessel according to the centerline of the blood vessel comprises:

obtaining a centerline of the straightened blood vessel by straightening the centerline of the blood vessel;

dividing a blood vessel partial area image into x units along a blood vessel extension direction from a starting point to an ending point, where x is a positive integer;

setting a centerline of blood vessel of each of the units correspondingly along the centerline of the straightened blood vessel;

making an image after correspondingly setting as an image of a straightened blood vessel.

Optionally, in the above method for acquiring a contour line of a blood vessel according to a centerline of the blood vessel, a manner for making the preset contour line of the blood vessel step-by-step approach the centerline of the straightened blood vessel to acquire a contour line of the straightened blood vessel comprises:

dividing the preset contour line of the blood vessel into y units, where y is a positive integer;

acquiring z points located on each preset contour line of the blood vessel from each of the units;

making the z points respectively approach the centerline of the straightened blood vessel in a graded manner along a direction perpendicular to the centerline of the straightened blood vessel to generate z approaching points, where z is a positive integer;

setting a RGB difference threshold as $\Delta RGB_{threshold}$, comparing an RGB value of the approaching point with an RGB value of a point on the straight center line of the blood vessel at each approach along the direction perpendicular to the centerline of the straightened blood vessel, and stopping the approach of the approaching point to the centerline of the straightened blood vessel when the difference is less than or equal to $\Delta RGB_{threshold}$;

acquiring the approaching points as contour points;

obtaining a smooth curve formed by sequentially connecting the contour points as a contour line of the straightened blood vessel.

Optionally, in the above method for acquiring a contour line of a blood vessel according to a centerline of the blood vessel, a manner for extracting a centerline of a blood vessel according to a two-dimensional coronary artery angiogram image comprises:

reading a two-dimensional coronary angiogram image;

acquiring a blood vessel segment of interest;

picking a starting point, a seed point and an ending point of the blood vessel segment of interest;

segmenting the two-dimensional angiogram image between two adjacent points of the starting point, the seed point and the ending point, respectively, to obtain at least two blood vessel partial area images;

extracting at least one blood vessel partial path line from each of the blood vessel partial area images;

connecting corresponding blood vessel partial path lines on each of the blood vessel partial area images to obtain at least one path line of the blood vessel;

selecting one path line of the blood vessel as a centerline of the blood vessel.

Optionally, in the above method for acquiring a contour line of a blood vessel according to a centerline of the blood vessel, a manner for extracting at least one blood vessel local path line respectively from the blood vessel partial area images comprises:

performing image enhancement processing for the blood vessel partial area images to obtain a sharply-contrasting rough image of the blood vessel;

meshing the rough image of the blood vessel, and extracting at least one blood vessel local path line along a direction from the starting point to the ending point.

Optionally, in the above method for acquiring a contour line of a blood vessel according to a centerline of the blood vessel, a manner for performing image enhancement processing for the blood vessel partial area images to obtain a sharply-contrasting rough image of the blood vessel comprises:

using the blood vessel segment of interest as a foreground and other areas as a background in each of the blood vessel partial area images, and enhancing the foreground and weakening the background to obtain a sharply-contrasting rough image of the blood vessel.

Optionally, the above method for acquiring a contour line of a blood vessel according to a centerline of the blood vessel, a manner for meshing the rough image of the blood vessel and extracting at least one blood vessel local path line along a direction from the starting point to the ending point comprises:

meshing the rough image of the blood vessel;

along a blood vessel extension direction from the starting point to the ending point, searching for a point having a shortest path in time with the starting point as a second point from intersecting points of surrounding n meshes, and searching for a point having a shortest path in time with the second point as a third point from intersecting points of surrounding n meshes, and repeating the above step for the third point until the shortest path in time reaches the ending point, where n is a positive integer greater than or equal to 1;

obtaining at least one blood vessel local path line by connecting a line extending from the starting point to the ending point according to the searching sequence.

Optionally, in the above method for acquiring a contour line of a blood vessel according to a centerline of the blood vessel, a manner for selecting one path line of the blood vessel as a centerline of the blood vessel comprises:

summing a time taken for each path line of the blood vessel extending from the starting point to the ending point if there are two or more path lines of the blood vessel;

selecting the path line of the blood vessel with the shortest time as a centerline of the blood vessel.

In a second aspect, the present disclosure provides an apparatus for acquiring a contour line of a blood vessel according to a centerline of the blood vessel, comprising: a centerline extraction unit, a straightening unit, a first blood vessel contour line unit, and a second blood vessel contour line unit connected in sequence;

the centerline extraction unit is configured to extract a centerline of a blood vessel according to a two-dimensional coronary angiogram image;

the straightening unit is configured to obtain an image of a straightened blood vessel according to the centerline of the blood vessel extracted by the centerline extraction unit;

the first blood vessel contour line unit is configured to set a threshold $D_{threshold}$ for a diameter of the blood vessel on the image of the straightened blood vessel sent by the straightening unit, to generate a preset contour line of the blood vessel on both sides of a centerline of the straightened blood vessel according to the $D_{threshold}$, and to make the preset contour line of the blood vessel step-by-step approach the centerline of the straightened blood vessel to acquire a contour line of the straightened blood vessel;

the second blood vessel contour line unit is configured to project the contour line of the straightened blood vessel sent by the first blood vessel contour line unit back onto the image of the centerline of the blood vessel to obtain a contour line of the blood vessel.

Optionally, in the above apparatus for acquiring a contour line of a blood vessel according to a centerline of the blood vessel, the straightening unit comprises: a centerline straightening module, an area dividing module and a straightened blood vessel image module connected in sequence;

the centerline straightening module is configured to obtain a centerline of the straightened blood vessel by straightening the centerline of the blood vessel;

the area dividing module is configured to divide a blood vessel partial area image into x units along a blood vessel extension direction from a starting point to an ending point, where x is a positive integer;

the straightened blood vessel image module is configured to set a centerline of blood vessel of each of the units correspondingly along the centerline of the straightened blood vessel, and to make an image after correspondingly setting as an image of a straightened blood vessel.

Optionally, in the above apparatus for acquiring a contour line of a blood vessel according to a centerline of the blood vessel, the first blood vessel contour line unit further comprises: a contour line dividing module, a contour point extraction module and a straightened blood vessel contour line module connected in sequence;

the contour line dividing module is connected with the straightened blood vessel image module and is configured to set a threshold $D_{threshold}$ for a diameter of the blood vessel on the image of the straightened blood vessel, to generate a preset contour line of the blood vessel on both sides of a centerline of the straightened blood vessel according to the $D_{threshold}$; and to divide the preset contour line of the blood vessel into y units, where y is a positive integer;

the contour point extraction module is configured to acquiring z points located on each preset contour line of the blood vessel from each of the units according to the y units sent by the contour line dividing module; to make the z points respectively approach the centerline of the straightened blood vessel in a graded manner along a direction perpendicular to the centerline of the straightened blood vessel to generate z approaching points, where z is a positive integer; to set a RGB difference threshold as $\Delta RGB_{threshold}$, comparing an RGB value of the approaching point with an RGB value of a point on the straight center line of the blood vessel at each approach along the direction perpendicular to the centerline of the straightened blood vessel, and to stop the approach of the approaching point to the centerline of the straightened blood vessel when the difference is less than or equal to $\Delta RGB_{threshold}$; to acquire the approaching points as contour points;

the straightened blood vessel contour line module is configured to obtain a smooth curve formed by sequentially connecting the contour points sent by the contour point extraction module as a contour line of the straightened blood vessel.

In a third aspect, the present disclosure provides a coronary artery analysis system comprising the above apparatus for acquiring a contour line of a blood vessel according to a centerline of the blood vessel.

In a fourth aspect, the present disclosure provides a computer storage medium having stored thereon a computer program to be executed by a processor, wherein the above method for acquiring a contour line of a blood vessel according to a centerline of the blood vessel is implemented when the computer program is executed by the processor.

The beneficial effects brought about by the solutions provided by the embodiments of the present disclosure comprise at least:

The disclosure provides a method for extracting a centerline of a blood vessel according to a two-dimensional coronary artery angiogram image; obtaining an image of a straightened blood vessel according to the centerline of the blood vessel; setting a threshold $D_{threshold}$ for a diameter of the blood vessel on the image of the straightened blood vessel; generating a preset contour line of the blood vessel on both sides of a centerline of the straightened blood vessel according to the $D_{threshold}$; making the preset contour line of the blood vessel step-by-step approach the centerline of the straightened blood vessel to acquire a contour line of the straightened blood vessel; projecting the contour line of the straightened blood vessel back onto the image of the centerline of the blood vessel to obtain a contour line of the blood vessel. The extraction of the contour line of the blood vessel is quick and accurate.

BRIEF DESCRIPTION OF THE DRAWINGS

The drawings illustrated here are used to provide a further understanding of the present disclosure and constitute a part of the present disclosure. The exemplary embodiments and the descriptions thereof are used to explain the present disclosure, and do not constitute an improper limitation on the present disclosure. In the drawings.

The reference signs are described below:

centerline extraction unit 100, straightening unit 200, centerline straightening module 210, area dividing module 220, straightened blood vessel image module 230, first blood vessel contour line unit 300, contour line dividing module 310, contour point extraction module 320, straightened blood vessel contour line module 330, and second blood vessel contour line unit 400.

DETAILED DESCRIPTION OF PREFERRED EMBODIMENTS

In order to make objects, technical solutions and advantages of the present disclosure clearer, the technical solutions of the present disclosure will be clearly and completely described below with reference to the specific embodiments and corresponding drawings. It is apparent that the described embodiments are merely part of the embodiments of the present disclosure rather than all of them. Based on the embodiments in the present disclosure, without making creative work, all the other embodiments obtained by a person skilled in the art will fall into the protection scope of the present disclosure.

Hereinafter, a number of embodiments of the present disclosure will be disclosed with drawings. For clear illustration, many practical details will be described in the following description. However, it should be understood that the present disclosure should not be limited by these practical details. In other words, in some embodiments of the present disclosure, these practical details are unnecessary. In addition, in order to simplify the drawings, some conventionally used structures and components will be shown in simple schematic ways in the drawings.

In the prior art, when calculating blood vessel evaluation parameters through a three-dimensional model of a blood vessel, it is often necessary to extract a contour line of the blood vessel. Due to the presence of curling and unclear edges of the blood vessel, it is particularly difficult to extract the contour line of the blood vessel, and calculation data is large and tedious. Therefore, how to quickly extract the contour line of the blood vessel and how to improve the accuracy of extraction have always been problems that need to be solved by those skilled in the art.

Embodiment 1

Figure 1:
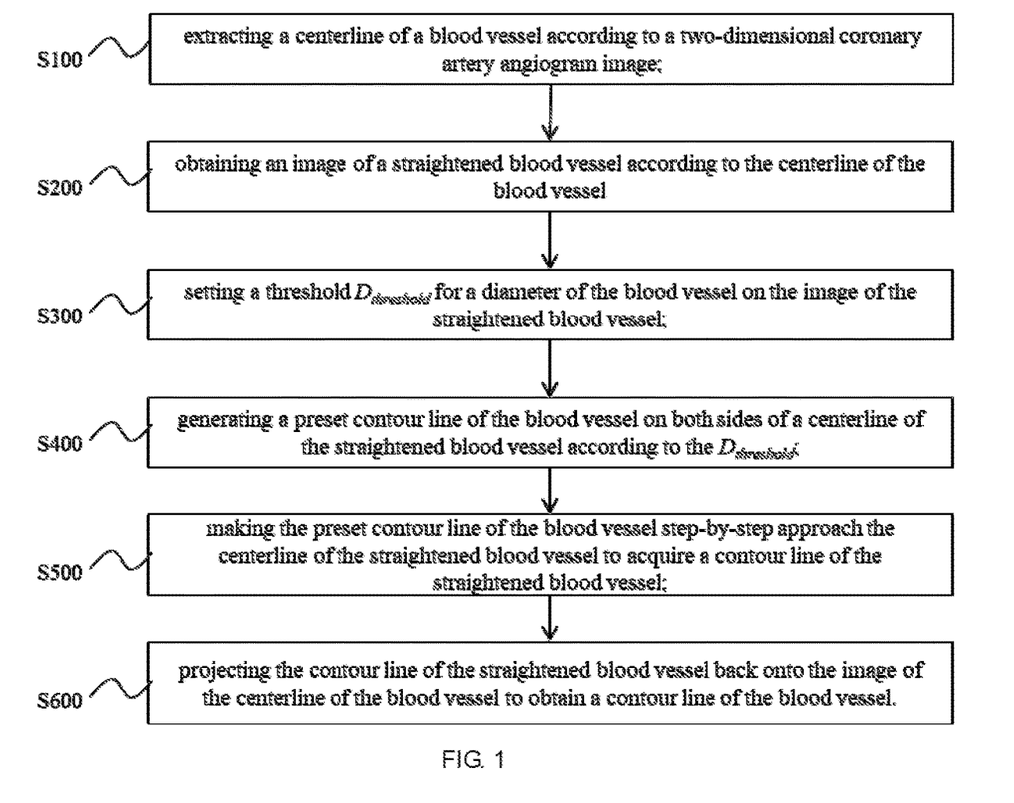
FIG. 1 is a flowchart of Embodiment 1 of a method for acquiring a contour line of a blood vessel according to a centerline of the blood vessel of the present disclosure.
Figure 2:
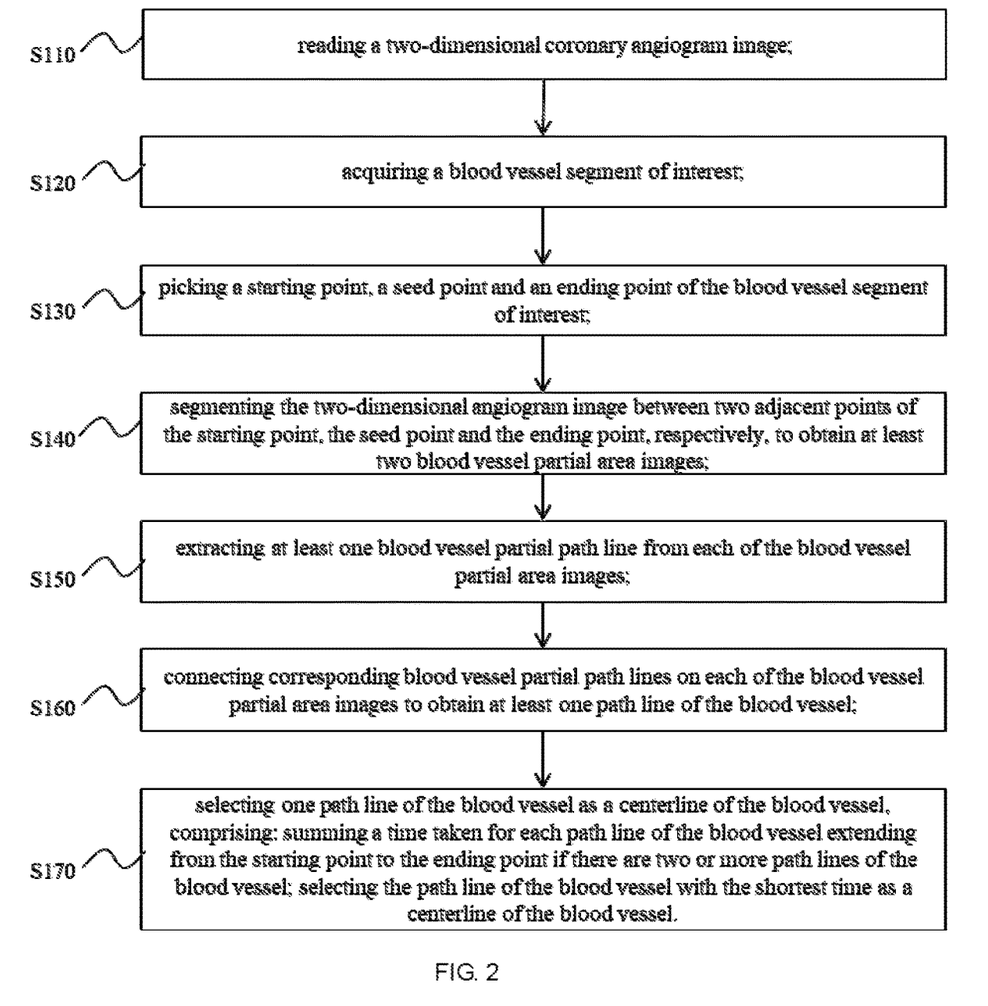
FIG. 2 is a flow chart of S100 of the present disclosure.
Figure 3:
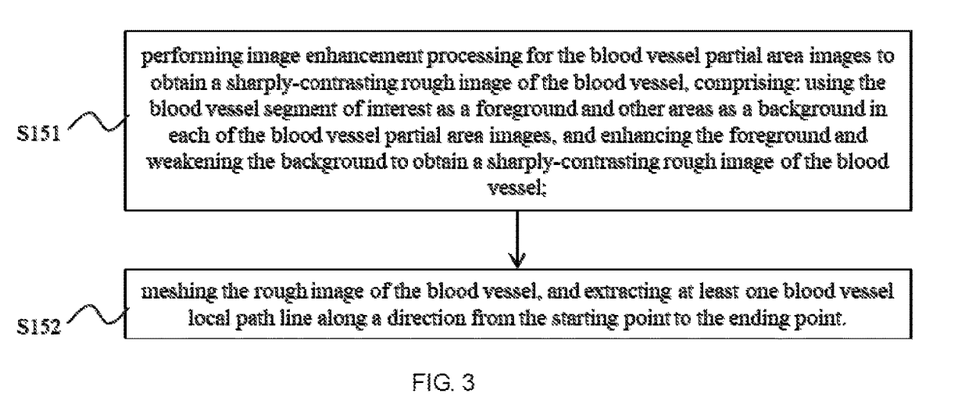
FIG. 3 is a flowchart of S150 of the present disclosure.
Figure 4:
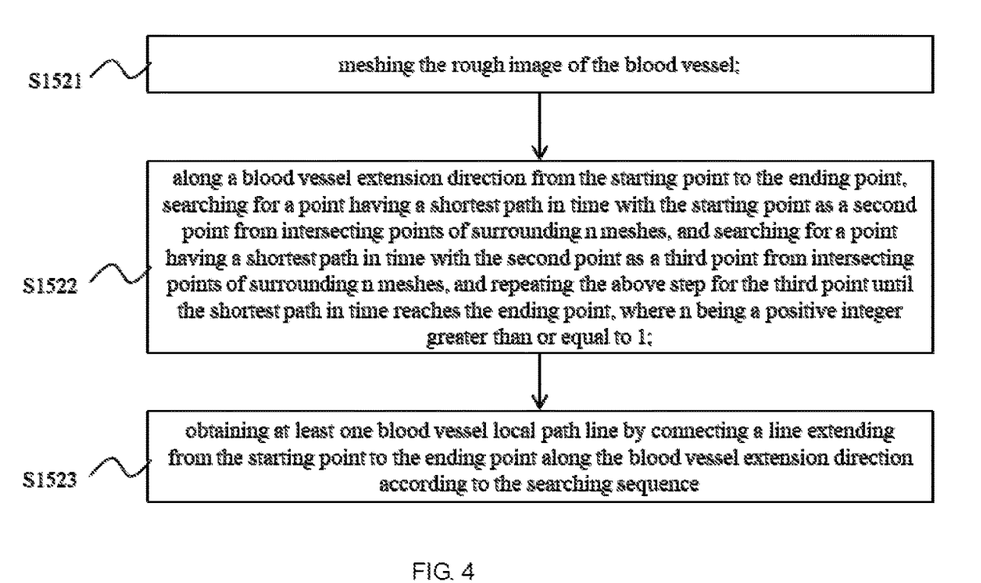
FIG. 4 is a flowchart of S152 of the present disclosure.
Figure 5:
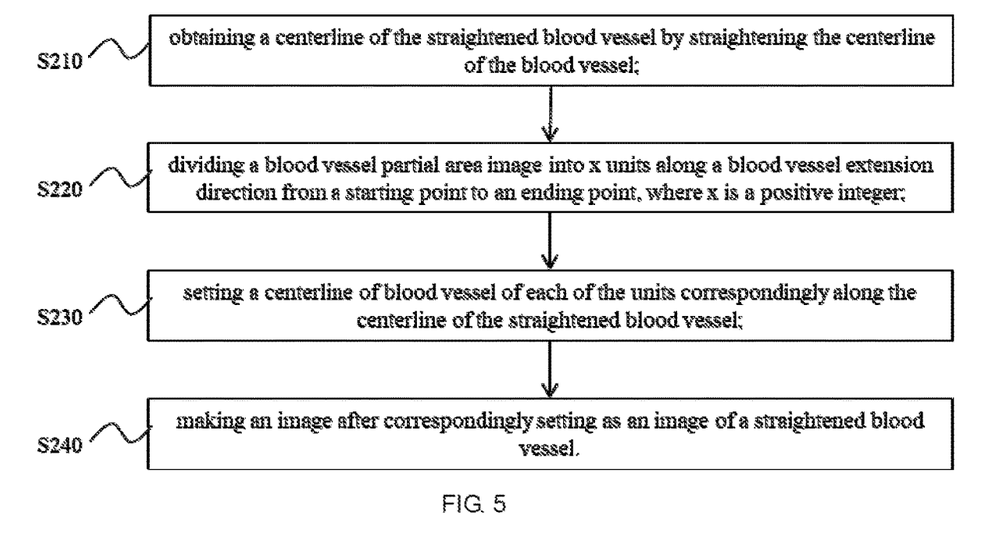
FIG. 5 is a flow chart of S200 of the present disclosure.
Figure 6:
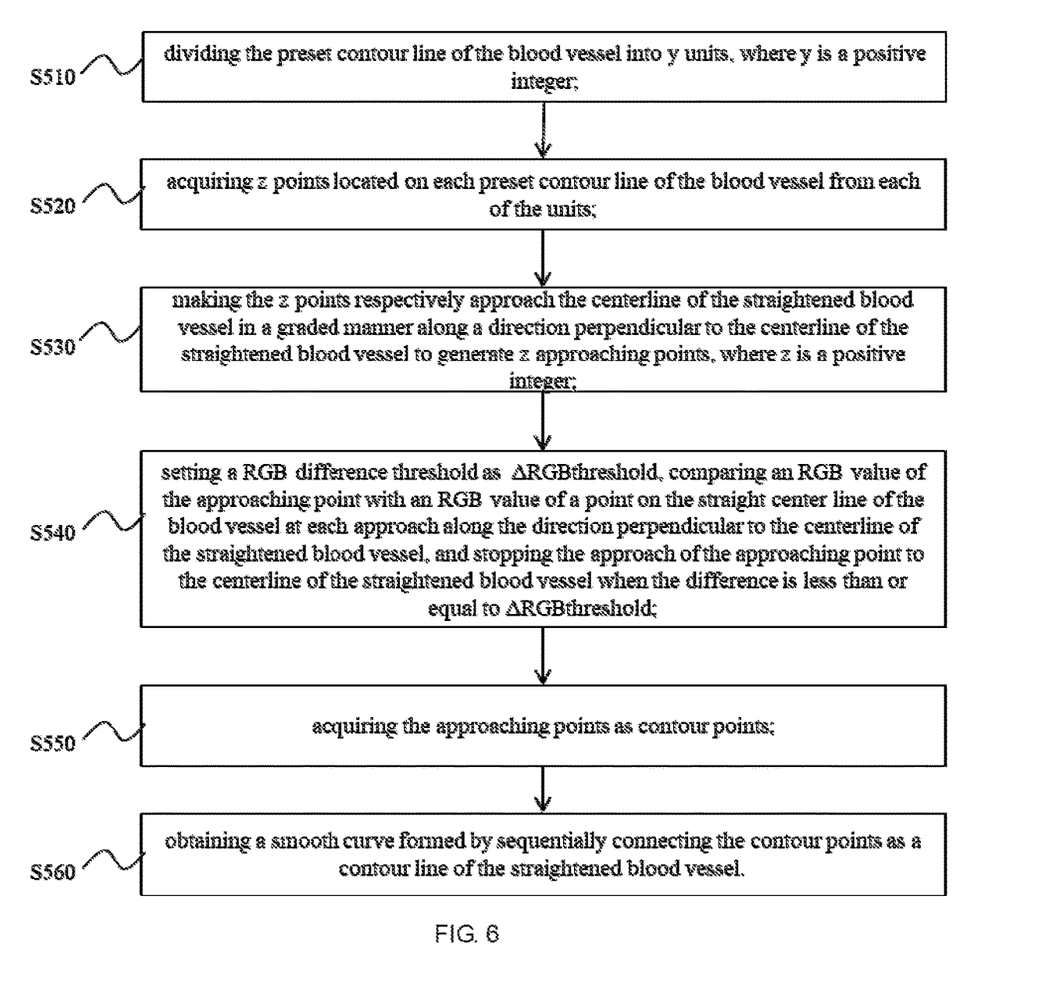
FIG. 6 is a flow chart of S500 of the present disclosure.

As shown in FIG. 1, in order to solve the above problems, the present disclosure provides a method for acquiring a contour line of a blood vessel according to a centerline of the blood vessel, comprising:

S100, extracting a centerline of a blood vessel according to a two-dimensional coronary artery angiogram image, as shown in FIG. 2, comprising:

S110, reading a two-dimensional coronary angiogram image;

S120, acquiring a blood vessel segment of interest;

S130, picking a starting point, a seed point and an ending point of the blood vessel segment of interest; the seed point is configured to improve the accuracy of the calculation, so it is also possible to use only the starting point and the ending point when the picking is relatively accurate;

S140: segmenting the two-dimensional angiogram image between two adjacent points of the starting point, the seed point and the ending point, respectively, to obtain at least two blood vessel partial area images; preferably, the blood vessel partial area images are rectangular images; since the calculation is done only for each blood vessel partial area, the complexity and tediousness of calculation is reduced, the speed of calculation is increased, and the design is scientific;

S150, extracting at least one blood vessel partial path line from each of the blood vessel partial area images, as shown in FIG. 3, comprising:

S151, performing image enhancement processing for the blood vessel partial area images to obtain a sharply-contrasting rough image of the blood vessel, comprising: using the blood vessel segment of interest as a foreground and other areas as a background in each of the blood vessel partial area images, and enhancing the foreground and weakening the background to obtain a sharply-contrasting rough image of the blood vessel;

S152, meshing the rough image of the blood vessel, and extracting at least one blood vessel local path line along a direction from the starting point to the ending point, as shown in FIG. 4, comprising:

S1521, meshing the rough image of the blood vessel;

S1522, along a blood vessel extension direction from the starting point to the ending point, searching for a point having a shortest path in time with the starting point as a second point from intersecting points of surrounding n meshes, and searching for a point having a shortest path in time with the second point as a third point from intersecting points of surrounding n meshes, and repeating the above step for the third point until the shortest path in time reaches the ending point, where n is a positive integer greater than or equal to 1;

S1523, obtaining at least one blood vessel local path line by connecting a line extending from the starting point to the ending point according to the searching sequence;

S160, connecting corresponding blood vessel partial path lines on each of the blood vessel partial area images to obtain at least one path line of the blood vessel;

S170, selecting one path line of the blood vessel as a centerline of the blood vessel, comprising: summing a time taken for each path line of the blood vessel extending from the starting point to the ending point if there are two or more path lines of the blood vessel; selecting the path line of the blood vessel with the shortest time as a centerline of the blood vessel;

S200, obtaining an image of a straightened blood vessel according to the centerline of the blood vessel, as shown in FIG. 5, comprising:

S210, obtaining a centerline of the straightened blood vessel by straightening the centerline of the blood vessel;

S220, dividing a blood vessel partial area image into x units along a blood vessel extension direction from a starting point to an ending point, where x is a positive integer;

S230, setting a centerline of blood vessel of each of the units correspondingly along the centerline of the straightened blood vessel;

S240, making an image after correspondingly setting as an image of a straightened blood vessel;

S300, setting a threshold $D_{threshold}$ for a diameter of the blood vessel on the image of the straightened blood vessel;

S400, generating a preset contour line of the blood vessel on both sides of a centerline of the straightened blood vessel according to the $D_{threshold}$;

S500, making the preset contour line of the blood vessel step-by-step approach the centerline of the straightened blood vessel to acquire a contour line of the straightened blood vessel, as shown in FIG. 6, comprising:

S510, dividing the preset contour line of the blood vessel into y units, where y is a positive integer;

S520, acquiring z points located on each preset contour line of the blood vessel from each of the units;

S530, making the z points respectively approach the centerline of the straightened blood vessel in a graded manner along a direction perpendicular to the centerline of the straightened blood vessel to generate z approaching points, where z is a positive integer;

S540, setting a RGB difference threshold as $\Delta RGB_{threshold}$, comparing an RGB value of the approaching point with an RGB value of a point on the straight center line of the blood vessel at each approach along the direction perpendicular to the centerline of the straightened blood vessel, and stopping the approach of the approaching point to the centerline of the straightened blood vessel when the difference is less than or equal to $\Delta RGB_{threshold}$;

S550, acquiring the approaching points as contour points;

S560, obtaining a smooth curve formed by sequentially connecting the contour points as a contour line of the straightened blood vessel;

S600, projecting the contour line of the straightened blood vessel back onto the image of the centerline of the blood vessel to obtain a contour line of the blood vessel.

Embodiment 2

Figure 7:
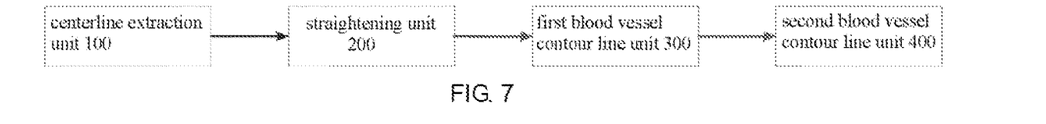
FIG. 7 is a structural block diagram of an embodiment of an apparatus for acquiring a contour line of a blood vessel according to a centerline of the blood vessel of the present disclosure.

As shown in FIG. 7, the present disclosure provides an apparatus for acquiring a contour line of a blood vessel according to a centerline of the blood vessel, comprising: a centerline extraction unit 100, a straightening unit 200, a first blood vessel contour line unit 300 and a second blood vessel contour line unit 400 connected in sequence; the centerline extraction unit 100 is configured to extract a centerline of a blood vessel according to a two-dimensional coronary angiogram image; the straightening unit 200 is configured to obtain an image of a straightened blood vessel according to the centerline of the blood vessel extracted by the centerline extraction unit 100; the first blood vessel contour line unit 300 is configured to set a threshold $D_{threshold}$ for a diameter of the blood vessel on the image of the straightened blood vessel sent by the straightening unit 200, and to generate a preset contour line of the blood vessel on both sides of a centerline of the straightened blood vessel according to the $D_{threshold}$ and make the preset contour line of the blood vessel step-by-step approach the centerline of the straightened blood vessel to acquire a contour line of the straightened blood vessel; the second blood vessel contour line unit 400 is configured to project the contour line of the straightened blood vessel sent by the first blood vessel contour line unit 300 back onto the image of the centerline of the blood vessel to obtain a contour line of the blood vessel.

Figure 8:
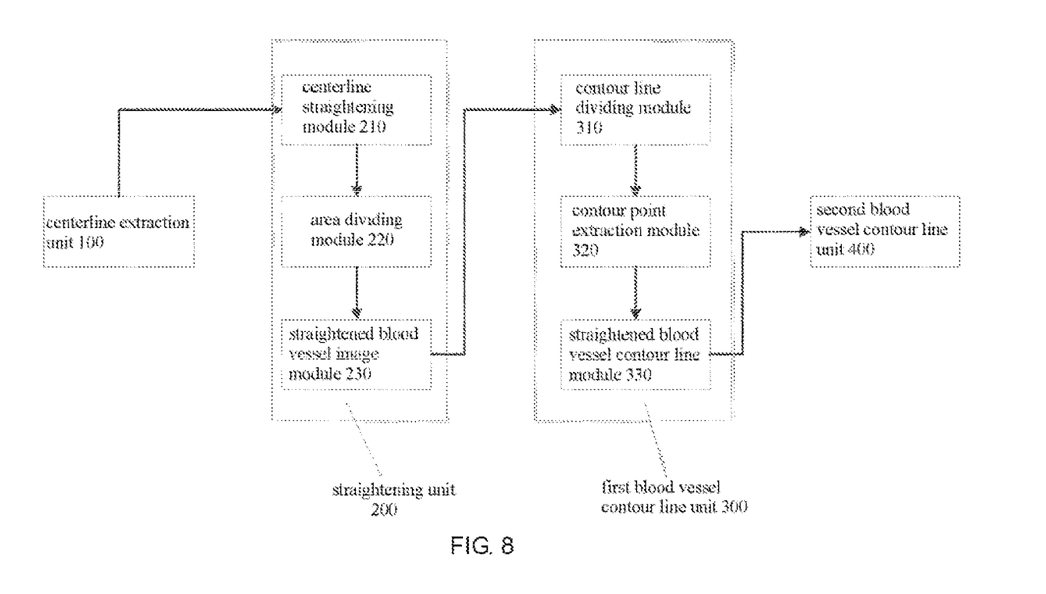
FIG. 8 is a structural block diagram of another embodiment of an apparatus for acquiring a contour line of a blood vessel according to a centerline of the blood vessel of the present disclosure.

As shown in FIG. 8, in an embodiment of the present disclosure, the straightening unit 200 comprises: a centerline straightening module 210, an area dividing module 220 and a straightened blood vessel image module 230 connected in sequence; the centerline straightening module 210 is configured to obtain a centerline of the straightened blood vessel by straightening the centerline of the blood vessel; the area dividing module 220 is configured to divide a blood vessel partial area image into x units along a blood vessel extension direction from a starting point to an ending point, where x is a positive integer; the straightened blood vessel image module 230 is configured to set a centerline of blood vessel of each of the units correspondingly along the centerline of the straightened blood vessel, and to make an image after correspondingly setting as an image of a straightened blood vessel.

As shown in FIG. 8, in an embodiment of the present disclosure, the first blood vessel contour line unit 300 further comprises: a contour line dividing module 310, a contour point extraction module 320 and a straightened blood vessel contour line module 330 connected in sequence; the contour line dividing module 310 is connected with the straightened blood vessel image module 230 and is configured to set a threshold $D_{threshold}$ for a diameter of the blood vessel on the image of the straightened blood vessel, to generate a preset contour line of the blood vessel on both sides of a centerline of the straightened blood vessel according to the $D_{threshold}$; and to divide the preset contour line of the blood vessel into y units, where y is a positive integer; the contour point extraction module 320 is configured to acquiring z points located on each preset contour line of the blood vessel from each of the units according to the y units sent by the contour line dividing module; to make the z points respectively approach the centerline of the straightened blood vessel in a graded manner along a direction perpendicular to the centerline of the straightened blood vessel to generate z approaching points, where z is a positive integer; to set a RGB difference threshold as $\Delta RGB_{threshold}$, comparing an RGB value of the approaching point with an RGB value of a point on the straight center line of the blood vessel at each approach along the direction perpendicular to the centerline of the straightened blood vessel, and to stop the approach of the approaching point to the centerline of the straightened blood vessel when the difference is less than or equal to $\Delta RGB_{threshold}$; to acquire the approaching points as contour points; the straightened blood vessel contour line module 330 is configured to obtain a smooth curve formed by sequentially connecting the contour points sent by the contour point extraction module as a contour line of the straightened blood vessel.

The present disclosure provides a coronary artery analysis system, comprising: the above apparatus for acquiring a contour line of a blood vessel according to a centerline of the blood vessel.

The present disclosure provides a computer storage medium having stored thereon a computer program to be executed by a processor, wherein the above method for acquiring a contour line of a blood vessel according to a centerline of the blood vessel is implemented when the computer program is executed by the processor.

A person skilled in the art knows that various aspects of the present disclosure can be implemented as a system, a method, or a computer program product. Therefore, each aspect of the present disclosure can be specifically implemented in the following forms, namely: complete hardware implementation, complete software implementation (including firmware, resident software, microcode, etc.), or a combination of hardware and software implementations, which here can be collectively referred to as "circuirt", "module" or "system". In addition, in some embodiments, various aspects of the present disclosure may also be implemented in the form of a computer program product in one or more computer-readable media, and the computer-readable medium contains computer-readable program code. Implementation of a method and/or a system of embodiments of the present disclosure may involve performing or completing selected tasks manually, automatically, or a combination thereof.

For example, hardware for performing selected tasks according to the embodiment(s) of the present disclosure may be implemented as a chip or a circuit. As software, selected tasks according to the embodiment(s) of the present disclosure can be implemented as a plurality of software instructions executed by a computer using any suitable operating system. In the exemplary embodiment(s) of the present disclosure, a data processor performs one or more tasks according to the exemplary embodiment(s) of a method and/or system as described herein, such as a computing platform for executing multiple instructions. Optionally, the data processor comprises a volatile memory for storing instructions and/or data, and/or a non-volatile memory for storing instructions and/or data, for example, a magnetic hard disk and/or movable medium. Optionally, a network connection is also provided. Optionally, a display and/or user input device, such as a keyboard or mouse, are/is also provided.

Any combination of one or more computer readable media can be utilized. The computer-readable medium may be a computer-readable signal medium or a computer-readable storage medium. The computer-readable storage medium may be, for example, but not limited to, an electrical, magnetic, optical, electromagnetic, infrared, or semiconductor system, apparatus, or device, or any combination of the above. More specific examples (non-exhaustive list) of computer-readable storage media would include the following:

Electrical connection with one or more wires, portable computer disk, hard disk, random access memory (RAM), read only memory (ROM), erasable programmable read only memory (EPROM or flash memory), optical fiber, portable compact disk read only memory (CD-ROM), optical storage device, magnetic storage device, or any suitable combination of the above. In this document, the computer-readable storage medium can be any tangible medium that contains or stores a program, and the program can be used by or in combination with an instruction execution system, apparatus, or device.

The computer-readable signal medium may include a data signal propagated in baseband or as a part of a carrier wave, which carries computer-readable program code. This data signal for propagation can take many forms, including but not limited to electromagnetic signals, optical signals, or any suitable combination of the above. The computer-readable signal medium may also be any computer-readable medium other than the computer-readable storage medium. The computer-readable medium can send, propagate, or transmit a program for use by or in combination with the instruction execution system, apparatus, or device.

The program code contained in the computer-readable medium can be transmitted by any suitable medium, including, but not limited to, wireless, wired, optical cable, RF, etc., or any suitable combination of the above.

For example, any combination of one or more programming languages can be used to write computer program codes for performing operations for various aspects of the present disclosure, including object-oriented programming languages such as Java, Smalltalk, C++, and conventional process programming languages, such as "C" programming language or similar programming language. The program code can be executed entirely on a user's computer, partly on a user's computer, executed as an independent software package, partly on a user's computer and partly on a remote computer, or entirely on a remote computer or server. In the case of a remote computer, the remote computer can be connected to a user's computer through any kind of network including a local area network (LAN) or a wide area network (WAN), or it can be connected to an external computer (for example, connected through Internet provided by an Internet service provider).

It should be understood that each block of the flowcharts and/or block diagrams and combinations of blocks in the flowcharts and/or block diagrams can be implemented by computer program instructions. These computer program instructions can be provided to the processor of general-purpose computers, special-purpose computers, or other programmable data processing devices to produce a machine, which produces a device that implements the functions/actions specified in one or more blocks in the flowcharts and/or block diagrams when these computer program instructions are executed by the processor of the computer or other programmable data processing devices.

It is also possible to store these computer program instructions in a computer-readable medium. These instructions make computers, other programmable data processing devices, or other devices work in a specific manner, so that the instructions stored in the computer-readable medium generate an article of manufacture comprising instructions for implementation of the functions/actions specified in one or more blocks in the flowcharts and/or block diagrams.

Computer program instructions can also be loaded onto a computer (for example, a coronary artery analysis system) or other programmable data processing equipment to facilitate a series of operation steps to be performed on the computer, other programmable data processing apparatus or other apparatus to produce a computer-implemented process, which enable instructions executed on a computer, other programmable device, or other apparatus to provide a process for implementing the functions/actions specified in the flowcharts and/or one or more block diagrams.

The above specific examples of the present disclosure further describe the purpose, technical solutions and beneficial effects of the present disclosure in detail. It should be understood that the above are only specific embodiments of the present disclosure and are not intended to limit the present disclosure. Within the spirit and principle of the present disclosure, any modification, equivalent replacement, improvement, etc. shall be included in the protection scope of the present disclosure.

What is claimed is:

1. A method for acquiring a contour line of a blood vessel according to a centerline of the blood vessel, comprising:
    extracting a centerline of a blood vessel according to a two-dimensional coronary artery angiogram image;
    obtaining an image of a straightened blood vessel according to the centerline of the blood vessel;
    setting a threshold $D_{threshold}$ for a diameter of the blood vessel on the image of the straightened blood vessel;
    generating a preset contour line of the blood vessel on both sides of a centerline of the straightened blood vessel according to the $D_{threshold}$;
    making the preset contour line of the blood vessel step-by-step approach the centerline of the straightened blood vessel to acquire a contour line of the straightened blood vessel;
    projecting the contour line of the straightened blood vessel back onto the image of the centerline of the blood vessel to obtain a contour line of the blood vessel.

2. The method for acquiring a contour line of a blood vessel according to a centerline of the blood vessel according to claim 1, wherein a manner for obtaining an image of a straightened blood vessel according to the centerline of the blood vessel comprises:
    obtaining a centerline of the straightened blood vessel by straightening the centerline of the blood vessel;
    dividing a blood vessel partial area image into x units along a blood vessel extension direction from a starting point to an ending point, where x is a positive integer;
    setting a centerline of blood vessel of each of the units correspondingly along the centerline of the straightened blood vessel;
    making an image after correspondingly setting as an image of a straightened blood vessel.

3. The method for acquiring a contour line of a blood vessel according to a centerline of the blood vessel according to claim 2, wherein a manner for making the preset contour line of the blood vessel step-by-step approach the centerline of the straightened blood vessel to acquire a contour line of the straightened blood vessel comprises:
    dividing the preset contour line of the blood vessel into y units, where y is a positive integer;
    acquiring z points located on each preset contour line of the blood vessel from each of the units;
    making the z points respectively approach the centerline of the straightened blood vessel in a graded manner along a direction perpendicular to the centerline of the straightened blood vessel to generate z approaching points, where z is a positive integer;
    setting a RGB difference threshold as $\Delta RGB_{threshold}$, comparing an RGB value of the approaching point with an RGB value of a point on the straight center line of the blood vessel at each approach along the direction perpendicular to the centerline of the straightened blood vessel, and stopping the approach of the approaching point to the centerline of the straightened blood vessel when the difference is less than or equal to $\Delta RGB_{threshold}$;
    acquiring the approaching points as contour points;
    obtaining a smooth curve formed by sequentially connecting the contour points as a contour line of the straightened blood vessel.

4. The method for acquiring a contour line of a blood vessel according to a centerline of the blood vessel according to claim 2, wherein a manner for extracting a centerline of a blood vessel according to a two-dimensional coronary artery angiogram image comprises:
reading a two-dimensional coronary angiogram image;
acquiring a blood vessel segment of interest;
picking a starting point, a seed point and an ending point of the blood vessel segment of interest;
segmenting the two-dimensional angiogram image between two adjacent points of the starting point, the seed point and the ending point, respectively, to obtain at least two blood vessel partial area images;
extracting at least one blood vessel partial path line from each of the blood vessel partial area images;
connecting corresponding blood vessel partial path lines on each of the blood vessel partial area images to obtain at least one path line of the blood vessel;
selecting one path line of the blood vessel as a centerline of the blood vessel.

5. The method for acquiring a contour line of a blood vessel according to a centerline of the blood vessel according to claim 4, wherein a manner for extracting at least one blood vessel local path line from each of the blood vessel partial area images comprises:
performing image enhancement processing for the blood vessel partial area images to obtain a sharply-contrasting rough image of the blood vessel;
meshing the rough image of the blood vessel, and extracting at least one blood vessel local path line along a direction from the starting point to the ending point.

6. The method for acquiring a contour line of a blood vessel according to a centerline of the blood vessel according to claim 5, wherein a manner for performing image enhancement processing for the blood vessel partial area images to obtain a sharply-contrasting rough image of the blood vessel comprises:
using the blood vessel segment of interest as a foreground and other areas as a background in each of the blood vessel partial area images, and enhancing the foreground and weakening the background to obtain a sharply-contrasting rough image of the blood vessel.

7. The method for acquiring a contour line of a blood vessel according to a centerline of the blood vessel according to claim 5, wherein a manner for meshing the rough image of the blood vessel and extracting at least one blood vessel local path line along a direction from the starting point to the ending point comprises:
meshing the rough image of the blood vessel;
along a blood vessel extension direction from the starting point to the ending point, searching for a point having a shortest path in time with the starting point as a second point from intersecting points of surrounding n meshes, and searching for a point having a shortest path in time with the second point as a third point from intersecting points of surrounding n meshes, and repeating the above step for the third point until the shortest path in time reaches the ending point, where n is a positive integer greater than or equal to 1;
obtaining at least one blood vessel local path line by connecting a line extending from the starting point to the ending point according to the searching sequence.

8. The method for acquiring a contour line of a blood vessel according to a centerline of the blood vessel according to claim 7, wherein a manner for selecting one path line of the blood vessel as a centerline of the blood vessel comprises:
summing a time taken for each path line of the blood vessel extending from the starting point to the ending point if there are two or more path lines of the blood vessel;
selecting the path line of the blood vessel with the shortest time as a centerline of the blood vessel.

9. An apparatus for acquiring a contour line of a blood vessel according to a centerline of the blood vessel, used for the method for acquiring a contour line of a blood vessel according to a centerline of the blood vessel according to claim 1, comprising: a centerline extraction unit, a straightening unit, a first blood vessel contour line unit and a second blood vessel contour line unit connected in sequence;
the centerline extraction unit being configured to extract a centerline of a blood vessel according to a two-dimensional coronary angiogram image;
the straightening unit being configured to obtain an image of a straightened blood vessel according to the centerline of the blood vessel extracted by the centerline extraction unit;
the first blood vessel contour line unit being configured to set a threshold $D_{threshold}$ for a diameter of the blood vessel on the image of the straightened blood vessel sent by the straightening unit; to generate a preset contour line of the blood vessel on both sides of a centerline of the straightened blood vessel according to the $D_{threshold}$, to make the preset contour line of the blood vessel step-by-step approach the centerline of the straightened blood vessel to acquire a contour line of the straightened blood vessel;
the second blood vessel contour line unit being configured to project the contour line of the straightened blood vessel sent by the first blood vessel contour line unit back onto the image of the centerline of the blood vessel to obtain a contour line of the blood vessel.

10. The apparatus for acquiring a contour line of a blood vessel according to a centerline of the blood vessel according to claim 9, wherein the straightening unit comprises: a centerline straightening module, an area dividing module and a straightened blood vessel image module connected in sequence;
the centerline straightening module being configured to obtain a centerline of the straightened blood vessel by straightening the centerline of the blood vessel;
the area dividing module being configured to divide a blood vessel partial area image into x units along a blood vessel extension direction from a starting point to an ending point, where x is a positive integer;
the straightened blood vessel image module being configured to set a centerline of blood vessel of each of the units correspondingly along the centerline of the straightened blood vessel, and to make an image after correspondingly setting as an image of a straightened blood vessel.

11. The apparatus for acquiring a contour line of a blood vessel according to a centerline of the blood vessel according to claim 9, wherein the first blood vessel contour line unit further comprises: a contour line dividing module, a contour point extraction module and a straightened blood vessel contour line module connected in sequence;
the contour line dividing module being connected with the straightened blood vessel image module and being configured to set a threshold $D_{threshold}$ for a diameter of the blood vessel on the image of the straightened blood vessel, to generate a preset contour line of the blood vessel on both sides of a centerline of the straightened blood vessel according to the $D_{threshold}$, and to divide the preset contour line of the blood vessel into y units, where y is a positive integer;

the contour point extraction module being configured to acquiring z points located on each preset contour line of the blood vessel from each of the units according to the y units sent by the contour line dividing module; to make the z points respectively approach the centerline of the straightened blood vessel in a graded manner along a direction perpendicular to the centerline of the straightened blood vessel to generate z approaching points, where z is a positive integer; to set a RGB difference threshold as $\Delta RGB_{threshold}$, comparing an RGB value of the approaching point with an RGB value of a point on the straight center line of the blood vessel at each approach along the direction perpendicular to the centerline of the straightened blood vessel, and to stop the approach of the approaching point to the centerline of the straightened blood vessel when the difference is less than or equal to $\Delta RGB_{threshold}$, to acquire the approaching points as contour points;

the straightened blood vessel contour line module being configured to obtain a smooth curve formed by sequentially connecting the contour points sent by the contour point extraction module as a contour line of the straightened blood vessel.

12. A coronary artery analysis system, comprising: the apparatus for acquiring a contour line of a blood vessel according to a centerline of the blood vessel according to claim 9.

13. A non-transitory computer storage medium having stored thereon a computer program to be executed by a processor, wherein the method for acquiring a contour line of a blood vessel according to a centerline of the blood vessel according to claim 1 is implemented when the computer program is executed by the processor.

* * * * *